(12) United States Patent
Paull et al.

(10) Patent No.: US 9,155,760 B2
(45) Date of Patent: Oct. 13, 2015

(54) METHOD OF PROPHYLAXIS OF BACTERIAL VAGINOSIS

(75) Inventors: Jeremy Robert Arthur Paull, Burwood (AU); Jacinth Kincaid Fairley, Hawthorn (AU); Clare Frances Price, Elsternwick (AU); Gareth Rhys Lewis, Cheltenham (AU)

(73) Assignee: STARPHARMA PTY LIMITED, Abbotsford, Victoria (AU)

( * ) Notice: Subject to any disclaimer, the term of this patent is extended or adjusted under 35 U.S.C. 154(b) by 0 days.

(21) Appl. No.: 13/472,953

(22) Filed: May 16, 2012

(65) Prior Publication Data

US 2012/0295839 A1    Nov. 22, 2012

Related U.S. Application Data

(63) Continuation-in-part of application No. PCT/AU2011/000891, filed on Jul. 14, 2011.

(60) Provisional application No. 61/486,700, filed on May 16, 2011.

(51) Int. Cl.
| | |
|---|---|
| *A61K 38/16* | (2006.01) |
| *A61P 31/04* | (2006.01) |
| *A61K 31/185* | (2006.01) |
| *A61P 31/18* | (2006.01) |
| *A61K 31/795* | (2006.01) |
| *A61K 9/00* | (2006.01) |

(52) U.S. Cl.
CPC ............ *A61K 31/795* (2013.01); *A61K 9/0034* (2013.01); *A61K 38/16* (2013.01)

(58) Field of Classification Search
CPC .................. A61K 47/48246; A61K 47/48315; A61K 38/16; A61K 31/185; A61P 31/04; A61P 31/22; A61P 31/10; A61P 31/18; A61P 31/20; A61P 15/02
See application file for complete search history.

(56) References Cited

U.S. PATENT DOCUMENTS

| | | | | |
|---|---|---|---|---|
| 6,426,067 | B1 * | 7/2002 | Matthews et al. | 424/78.08 |
| 6,464,971 | B1 * | 10/2002 | Matthews et al. | 424/78.17 |
| 7,572,459 | B2 * | 8/2009 | Matthews et al. | 424/405 |
| 7,589,056 | B2 * | 9/2009 | Matthews et al. | 514/1 |

FOREIGN PATENT DOCUMENTS

| | | | | |
|---|---|---|---|---|
| AU | WO 02/079299 | * | 10/2002 | C08G 69/48 |
| WO | WO 00/15240 | * | 3/2000 | A61K 31/47 |
| WO | 2002/079299 A1 | | 10/2002 | |

OTHER PUBLICATIONS

Jack D. Sobel. Vaginitis. Dec. 25, 1997. The New England Journal of Medicine, vol. 337, No. 26, 1896-1903.*
Rojo et al. Dendrimers and Dendritic Polymers as Anti-infective Agents: New Antimicrobial Strategies for Therapeutic Drugs. Anti-Infective Agents in Medicinal Chemistry, 2007, 6, 151-174.*
CDER/FDA. Guideline for Industry: Estimating the Maximum Safe Starting Dose in Initial Clinical Trials for Therapeutics in Adult Healthy Volunteers. Jul. 2005.*
Starpharma. VivaGel press release. Jul. 9, 2008.*
Starpharma. VivaGel press release. May 23, 2011.*
Rupp et al. VivaGel (SPL7013 Gel): a candidate dendrimer—microbicide for the prevention of HIV and HSV infection. Int J Nanomedicine. 2007; 2(4):561-6.*
Phillip Hay. Bacterial vaginosis. Medicine. 2005; 33(10):58-61.*
Larsson et al. Diagnosis of bacterial vaginosis: need forvalidation of microscopic image area used for scoring bacterial morphotypes. Sex Transm Infect 2004;80:63-67.*
Menjoge, et al., "Transport and biodistribution of dendrimers across human fetal membranes: Implications for intravaginal administraction of dendrimer-drug conjugates", Biomaterials, 2010, 31, 5007-5021.
Starpharma, AGM—Chairman and CEO presentations dated Nov. 12, 2009, 28 pages.
Starpharma, Starpharma receives FDA Clearance to commence Phase 2 Bacterial Vaginosis Study for VivaGel, dated Jul. 15, 2010, 3 pages.
Starpharma, Starpharma commences Phase 2 Bacterial Vaginosis study of VivaGel dated Aug. 16, 2010, 2 pages.
Starpharma, AGM Chairman and CEO presentations dated Nov. 11, 2010, 25 pages.
Clinical trial dose ranging study available on clinical trials. gov processed on Feb. 7, 2011, available online by Feb. 9, 2011, 4 pages.
Starpharma, Starpharma Interim Report and half-year financial results dated Feb. 21, 2011, 2 pages.
Starpharma, Starpharma presents at ASX Emerging Growth Conference dated Mar. 10, 2011, 25 pages.
Starpharma, Starpharma Completes Enrolment for Phase 2 Study of VivaGel for Treatment of BV date Mar. 23, 2011, 3 pages.
Starpharma, Shareholder Update, Broad appeal for Starpharma's dendrimer platform dated Mar. 2011, 4 pages.
Lackman-Smith, et al., "Development of a Comprehensive Human Immunodeficiency Virus Type 1 Screening Algorithm for Discovery and Preclinical Testing of Topical Microbicides", Antimicrobial Agents and Chemotherapy, vol. 52, No. 5, May 2008, pp. 1768-1781.
Patton, et al., "Preclinical Safety and Efficacy Assessments of Dendrimer-Based (SPL7013) Microbicide Gel Formulations in a Nonhuman Primate Model", Antimicrobial Agents and Chemotherapy, vol. 50, No. 5, May 2006, pp. 1696-1700.
Bourne, et al., "Dendrimers, a New Class of Candidate Topical Microbicides with Activity against Herpes Simplex Virus Infection", Antimicrobial Agents and Chemotherapy, vol. 44, No. 9, Sep. 2000, pp. 2471-2474.

(Continued)

*Primary Examiner* — Karlheinz R Skowronek
*Assistant Examiner* — Jia-Hai Lee
(74) *Attorney, Agent, or Firm* — Knobbe, Martens, Olson & Bear, LLP

(57) ABSTRACT

Methods of treatment or prophylaxis of bacterial vaginosis, prevention of recurrence of bacterial vaginosis and alleviation or prevention of symptoms or diagnostic criteria of bacterial vaginosis are provided. The methods include administration of an effective amount of a macromolecule comprising a polylysine, polyamidoamine, poly(etherhydroxyamine) or poly(propyleneimine) dendrimer and one or more sulfonic acid containing moieties attached thereto.

23 Claims, No Drawings

(56) References Cited

OTHER PUBLICATIONS

Jiang, et al., "SPL7013 Gel as a Topical Microbicide for Prevention of Vaginal Transmission of SHIV89.6P in Macaques", Aids Research and Human Retroviruses, vol. 21, No. 3, 2005, pp. 207-213.

Tyssen, et al., "Structure Activity Relationship of Dendrimer Microbicides with Dual Action Antiviral Activity David", PLoS ONE, vol. 5, Issue 8, e12309, doi:I0.1371journal.pone.OO12309, pp. 1-15.

Price, et al., "SPL7013 Gel (VivaGelH) Retains Potent HIV-1 and HSV-2 Inhibitory Activity following Vaginal Administration in Humans", PLoS ONE, vol. 6, Issue 9, e24095 doi: 10.1371journal.pone.0024095, pp. 1-12.

McCarthy, et al., "Dendrimers as Drugs: Discovery and Preclinical and Clinical Development of Dendrimer-Based Microbicides for HIV and STI Prevention", Molecular Pharmaceuticals, vol. 2, No. 4, pp. 312-318.

International Search Report and Opinion dated Aug. 22, 2011 for International Application No. PCT/AU2011/000891.

Bertrand, et al. "New pharmaceutical applications for macromolecular binders", Journal of Controlled Release 155 (2011) 200-210.

View of NCT01201057 on Mar. 25, 2011, Developed by the National Library of Medicine, ClinicalTrials.gov archive, Mar. 25, 2011.

Press report, May 12, 2008 retrievable from http://www.firstwordpharma.com/node/27585?tsid=17#axzz3QG2jhShc.

O'Loughlin, et al., "Safety, Tolerability, and Pharmacokinetics of SPL7013 Gel (VivaGel): A Dose Ranging, Phase I Study", Sexually Transmitted Diseases, 37(2), (2010), 100-104.

McGowan, et al. "Phase 1 randomized trial of the vaginal safety and acceptability of SPL7013 gel (VivaGel) in sexually active young women (MTN-004)", AIDS, 25, (2011) 1057-1064.

Gilbert Donders "Diagnosis and Management of Bacterial Vaginosis and Other Types of Abnormal Vaginal Bacterial Flora: A Review", CME Review Article, 65(7), 2010, 462-473.

Patton, et al., "A summary of preclinical topical microbicide vaginal safety and chlamydial efficacy evaluations in a pigtailed macaque model", Sex Trans Dis. Dec. 2008 v35, No. 12, 9 pages.

Cohen et al., "A phase I randomized placebo controlled trial of the safety of 3% SPL7013 gel (VivaGel) in health young women administered twice daily for 14 days", PLoS ONE, Jan. 2011, vol. 6, No. 1, e16258, 9 pages.

* cited by examiner

METHOD OF PROPHYLAXIS OF BACTERIAL VAGINOSIS

FIELD OF THE INVENTION

The present invention relates to a method of treatment or prophylaxis of bacterial vaginosis, or alleviation or prophylaxis of one or more symptoms of bacterial vaginosis. Methods of prophylaxis of recurrence of bacterial vaginosis are also described.

BACKGROUND OF THE INVENTION

Bacterial vaginosis (BV) is the most common vaginal infection worldwide and the most common cause of vaginal irritation, discharge and malodour. It is estimated that the prevalence of BV is about 30% in the United States, 44% in sub-Saharan Africa and about 10% in Australia. BV is linked to serious health problems such as preterm birth, post-operative infection and increased susceptibility to HIV and other sexually transmitted infections.

While BV has been studied for many years, its cause remains unknown and treatments available are not always effective. BV is characterized by an imbalance in vaginal flora in which normally plentiful *Lactobacillus* spp. are scarce and other anaerobic bacteria, such as *Gardnerella vaginalis, Mobiluncus* spp., *Atopobium vaginae* and *Prevotella* spp. are plentiful.

Current treatments recommended for treatment of BV include metronidazole, clindamycin and tinidazole. However, these treatments are becoming less effective because of resistant bacteria and also have significant side effects. Metronidazole and tinidazole carry a potential risk of carcinogenicity and also cause nausea, abdominal cramps, vomiting, headaches and flushing if alcohol is consumed during treatment or for up to three days after treatment. There is also a high incidence of fungal infection, such as *Candida albicans* (Thrush), during antibiotic treatment of BV. Furthermore, clindamycin creams are formulated with mineral oils unsuitable for use with latex condoms or other rubber products such as diaphragms and therefore may require abstinence from sexual intercourse during treatment to avoid pregnancy and/or infecting the sexual partner. There is a need for treatments that are not systemically absorbed and also minimize systemic or local adverse effects and are compatible with prophylactic devices such as condoms.

Some recognized difficulties with treatment of BV are that current antibiotic treatment does not always distinguish between the bacteria normally present in healthy vaginal flora and the infecting anaerobes, and not all anaerobes present are necessarily susceptible to the same antibiotic. There is a need for treatment for BV that has some selectivity for activity against unwanted bacteria and no or low activity against normal vaginal flora. In particular, there is a need for a treatment that reduces the levels of harmful Gram negative bacteria whilst not inhibiting re-establishment of *Lactobacillus* spp. such as lactic acid-producing or hydrogen peroxide-producing lactobacilli.

Another difficulty is that after treatment, BV often recurs. Based on the results of recent clinical trials, about two thirds of patients suffer from multiple episodes of BV. Since the prevalence of BV in the US is about 30%, this means 20% of women in the US have recurrent BV. Furthermore, recurrent treatment with antibiotics leads to increased incidence of antibiotic resistant bacteria and reduced effectiveness of treatment. There is currently no recommended therapeutic agent approved by the US FDA for prophylaxis of recurrence of BV. There is therefore a need for a therapy for prophylaxis of recurrence of BV.

SUMMARY OF THE INVENTION

The present invention is predicted at least in part on the observation that a dendrimer microbicidal agent has selective antibacterial activity against anaerobic bacteria such as *G. vaginalis* while having no or low antibacterial activity against normal vaginal *Lactobacillus* flora. It was also observed that the dendrimer microbicidal agent has particular activity when administered in an amount of 40 to 100 mg per day in a single dose.

In a first aspect there is provided a method of treatment or prophylaxis of BV in a subject, said method comprising administering to the subject an effective amount of a macromolecule comprising a polylysine, polyamidoamine, poly(etherhydroxylamine) or poly(propyleneimine) dendrimer of 1 to 5 generations and one or more sulfonic acid-containing moieties attached to one or more surface amino groups of the outermost generation of the dendrimer, wherein said effective amount is 40 to 100 mg of macromolecule per day.

In a particular embodiment, the effective amount is 40 to 60 mg per day. In some embodiments, the macromolecule is administered by vaginal administration.

In another aspect of the invention, there is provided a method of alleviation or prophylaxis of one or more symptoms of BV and/or one or more diagnostic criteria of BV in a subject, said method comprising administering to the subject an effective amount of a macromolecule comprising a polylysine, polyamidoamine, poly(etherhydroxylamine) or poly(propyleneimine) dendrimer of 1 to 5 generations and one or more sulfonic acid-containing moieties attached to one or more surface amino groups of the outermost generation of the dendrimer, wherein the one or more symptoms and diagnostic criteria are selected from:
  i) Nugent Score,
  ii) clue cells,
  iii) whiff test,
  iv) vaginal discharge,
  v) vaginal pH, and
  vi) malodour.

In some embodiments, two or more symptoms and/or diagnostic criteria are alleviated. In some embodiments, three or more symptoms and/or diagnostic criteria are alleviated.

In yet another aspect of the invention, there is provided a method of prophylaxis or reduction of recurrence of BV in a subject, said method comprising administering to the subject an effective amount of a macromolecule comprising a polylysine, polyamidoamine, poly(etherhydroxylamine) or poly(propyleneimine) dendrimer of 1 to 5 generations and one or more sulfonic acid-containing moieties attached to one or more surface amino groups of the outermost generation of the dendrimer, wherein said effective amount is administered 1 to 7 times per week.

In some embodiments, the administration is 3 to 4 days per week, such as on alternate days. In some embodiments, the administration is continued for a prolonged period, for example, months or years, such as up to 25 years. For example, in some embodiments, administration will continue for 1, 5, 10, 15 or 20 years.

In a further aspect there is provided a method of reducing the incidence of fungal infection or other microbial infection in a subject during or after treatment of BV comprising treating the BV by administering to the subject an effective amount of a macromolecule comprising a polylysine, polyamidoamine, poly(etherhydroxylamine) or poly(propyleneimine) dendrimer of 1 to 5 generations and one or more sulfonic acid-containing moieties attached to one or more surface amino groups of the outermost generation of the dendrimer.

In some embodiments, the incidence of thrush (candidiasis) seen with use of other antibiotics is reduced. In some embodiments, the effective amount is 40-100 mg per day in a single dose. In some embodiments, the macromolecule is administered by vaginal administration.

DESCRIPTION OF THE INVENTION

The singular forms "a", "an" and "the" include plural aspects unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "about" refers to a quantity, level, value, dimension, size or amount that varies by as much as 20%, 15%, 10% or 5% to a reference quantity, level, value, dimension, size or amount.

In one aspect, the present invention provides a method of treatment or prophylaxis of BV in a subject, said method comprising administering to the subject an effective amount of a macromolecule comprising a polylysine, polyamidoamine, poly(etherhydroxylamine) or poly(propyleneimine) dendrimer of 1 to 5 generations and having one or more sulfonic acid-containing moieties attached to one or more surface amino groups of the outermost generation of the dendrimer, wherein said effective amount is 40 mg to 100 mg of dendrimer per day.

In some embodiments, the effective amount is in the range of 40 to 90 mg per day, 40 to 80 mg per day, 40 to 70 mg per day, especially 40 to 60 mg per day and most especially about 50 mg per day.

In a particular embodiment, the macromolecule is formulated as a gel, especially a gel formulated with a pH between 4.5 and 5.5, especially about pH 5. Advantageously, this formulation may assist in reducing vaginal pH to between 4 and 5 or maintaining vaginal pH between 4 and 5. In some embodiments, the gel formulation of macromolecule comprises a rheology modifying agent, especially a Carbopol® polymer such as Carbopol® 971P. The rheology modifier may be present in an amount of 2-10%, especially about 5%. The gel formulation of macromolecule may also include a chelating agent, such as a polyaminocarboxylic acid. A particularly useful chelating agent is ethylenediamine tetraacetic acid (EDTA) and its salts. Suitable amounts of chelating agent are in the range of 0.001% to 2%, especially 0.005% to 1%. In some embodiments, the chelating agent is present in a low amount, such as 0.001% to 0.1%, especially about 0.005%. Other ingredients that may be included in the gel formulation include preservatives such as parabens, for example methylparaben and propylparaben or mixtures thereof, solvents such as water, pH adjusting agents such as hydroxide and emollients and humectants such as glycerine and propylene glycol.

In some embodiments, the macromolecule or a formulation of macromolecule is administered in multiple doses more than once per day, for example morning and night. In other embodiments, the macromolecule or formulation comprising the macromolecule is administered in a single dose once per day, for example, at night.

In some embodiments, the macromolecule or formulation comprising the macromolecule is administered vaginally. In some embodiments, the dosage may be administered in a volume of 3.5-5 grams, especially 4-5 grams and more especially about 5 grams, particularly when administered at night or immediately prior to the subject going to bed. The non-ambulating and predominantly horizontal position assumed during sleep assists in retention of the macromolecule formulation in the vagina increasing exposure time.

In some embodiments, the dosing occurs within proximity to sexual activity such as sexual intercourse, especially within 24 hours prior to or after intercourse, more especially within 3 hours prior to or after intercourse.

In some embodiments, the dosing occurs before, during or after menstruation, especially within 24 hours of the end of menstruation and more especially dosing is administered for 2, 3, 4 or 5 days after the end of menstruation. In some embodiments, the dosing occurs 1 to 3 days prior to anticipated onset of menstruation.

The term "treatment", as used herein, refers to at least partially attaining a desired therapeutic outcome. The therapeutic outcome may be a therapeutic cure at the end of treatment (EOT) or at a subsequent date after end of treatment (test of cure, TOC). The therapeutic outcome may be a clinical cure at EOT or TOC. The therapeutic outcome may be the alleviation of one or more symptoms of BV such as the alleviation of vaginal odour or vaginal discharge or may be reduction or normalization (or maintenance) of diagnostic criteria for BV such as vaginal pH, presence of clue cells or whiff test as defined by the Amsel criteria or by achieving a normal Nugent Score (Nugent Cure, <3).

The term "prophylaxis" refers to the prevention or delay of onset of BV in a subject at risk of contracting BV for the first time, or at risk of suffering recurrent episodes of BV. Those at risk of BV include women with multiple sexual partners or new sexual partners with a high frequency of vaginal intercourse. However, some studies have shown that sexual activity is not necessary for the development of BV (Yen et al., Obstet. Gynecol. 2003, 102: 927-933; Bump et al., Am. J. Obstet. Gynecol., 1988, 158: 935-939) and therefore BV is not necessarily considered a sexually transmitted infection. Some studies have also shown a high prevalence of BV in women who have sex with women (Marrazzo et al., J. Infect. Dis., 2002, 185: 1307-1313). In addition, studies show that 50% of women who have symptomatic BV and are treated with existing therapies experience a recurrent episode of BV within 6 months (Marrazzo et al., Sex. Trans. Dis., 2010, 37(12):732-744).

The term "prophylaxis" also refers to the prevention, delay or reduction in severity or frequency of one or more symptoms and/or one or more diagnostic criteria of BV in a subject at risk of contracting BV for the first time, or at risk of suffering recurrent episodes of BV.

The term "End of Treatment" (EOT) during acute treatment of an episode of BV refers to a period of 9 to 12 days after the first dose of therapy has been administered.

The term "Test of Cure" (TOC) during acute treatment of an episode of BV refers to a period of time after the last dose of therapy has been administered to assess whether relapse or recurrence has occurred. An example of Test of Cure may be 21 to 30 days after the first dose of therapy has been administered.

The term "Amsel's criteria" refers to the diagnostic criteria used to identify BV. These criteria include:
- homogenous white discharge that smoothly coats the vaginal mucosa;
- presence of clue cells (bacteria adhering to the vaginal epithelial cells, ≥20% of total cells on wet mount);
- vaginal pH of >4.5;
- positive whiff test (fishy odour with addition of 10% potassium hydroxide (KOH) to vaginal fluid).

In order for a clinical diagnosis of BV, three of the four Amsel's criteria must be present.

The term "Nugent Score" refers to a weighted score between 0 and 10 which is derived from a microbiological analysis using a Gram-stained vaginal smear (Nugent et al., 1991, J. Clin. Microbiol., 29(2): 297-301). The composite score is based on:
- Lactobacillus spp. morphotypes—0 (abundant)—4 (none)
- Gardnerella/Bacteroides spp. morphotypes—0 (none)—4 (abundant)
- Curved Gram-variable rods—0 (none)—2 (abundant)

A Nugent Score of 0-3 is considered normal, while a score of 4-6 (intermediate) is indicative of a disrupted vaginal microenvironment, and 7-10 is defined as BV. For the purposes of assessing a cure, the US Food and Drug Administration consider a score of 0-3 normal and 4-10 abnormal. The term "Nugent Score Cure" or "Nugent Cure" refers to a therapy resulting in a Nugent Score of 0-3.

The term "Clinical Cure" as used herein refers to the subject being asymptomatic and resolution of at least three of the four Amsel criteria at EOT and/or TOC. For example, at least three of a return to normal physiological discharge, a saline wet mount negative for clue cells, vaginal pH<4.7 and a negative whiff test occurs.

The term "Therapeutic Cure" refers to achieving both Clinical Cure and Nugent Cure after therapy.

As used herein, the term "Therapeutic Resolution" refers to achieving clinical cure and a Nugent Score of ≤6.

In some cases, a Clinical or Therapeutic Cure need not be achieved but one or more of the symptoms or diagnostic criteria apparent at the outset of treatment may be resolved. For example, the initial vaginal discharge may return to normal, the malodour associated with BV may be resolved, whiff test may be negative, vaginal pH may return to normal, clue cells may disappear or Nugent Score may become less than 4, while one or more other symptoms remain present. For example, Therapeutic Resolution may be achieved because the discharge, malodour and vaginal pH may be resolved but clue cells are still present and Nugent Score abnormal.

In another aspect of the invention, there is provided a method of alleviation or prophylaxis of one or more symptoms of BV and/or one or more diagnostic criteria of BV in a subject, said method comprising administering to the subject an effective amount of a macromolecule comprising a polylysine, polyamidoamine, poly(etherhydroxylamine) or poly(propyleneimine) dendrimer of 1 to 5 generations and having one or more sulfonic acid-containing moieties attached to one or more surface amino groups of the outermost generation of the dendrimer, wherein the one or more symptoms and diagnostic criteria are selected from:
i) Nugent Score,
ii) clue cells,
iii) whiff test,
iv) vaginal discharge
v) vaginal pH, and
vi) malodour.

In some embodiments, Nugent Score returns to the normal range (0-3). In some embodiments, the clue cells disappear. In some embodiments, malodour disappears. In some embodiments, vaginal discharge disappears. In some embodiments, vaginal pH returns to normal. In some embodiments, the whiff test is negative.

In some embodiments two, three or four of the symptoms or diagnostic criteria of BV are resolved, for example, Nugent Score and malodour; Nugent Score and whiff test; Nugent Score and clue cells; Nugent Score and vaginal discharge; Nugent Score and vaginal pH; clue cells and malodour; clue cells and whiff test; clue cells and vaginal discharge; clue cells and vaginal pH; malodour and whiff test; malodour and vaginal discharge; malodour and vaginal pH; vaginal discharge and vaginal pH; Nugent Score, malodour and clue cells, Nugent Score, malodour and vaginal discharge; Nugent Score, malodour and vaginal pH; Nugent Score, malodour and whiff test; Nugent Score, clue cells and vaginal discharge; Nugent Score, clue cells and vaginal pH; Nugent Score, vaginal discharge and vaginal pH; Nugent Score, vaginal discharge and whiff test; malodour, vaginal discharge and vaginal pH; malodour, vaginal discharge and whiff test; Nugent Score, clue cells, malodour and vaginal pH; Nugent Score, clue cells, malodour and vaginal discharge; Nugent Score, malodour, vaginal discharge and vaginal pH; Nugent Score, malodour, whiff test and vaginal discharge; Nugent Score, malodour, whiff test and vaginal pH; Nugent Score, clue cells, vaginal discharge and vaginal pH; Nugent Score, clue cells, whiff test and vaginal discharge; Nugent Score, clue cells, whiff test and vaginal pH; clue cells, malodour, whiff test and vaginal discharge; clue cells, malodour, whiff test and vaginal pH; and clue cells, malodour, vaginal discharge and vaginal pH.

In some embodiments, the effective amount is in the range of 15 to 1000 mg of macromolecule per day, especially 15 to 500 mg per day, 15 to 400 mg per day, 15 to 300 mg per day, 15 to 150 mg per day, 30 to 110 mg per day, 40 to 100 mg per day, 40 to 90 mg per day, 40 to 80 mg per day, 40 to 70 mg per day, more especially 40 to 60 mg per day, and most especially about 50 mg per day.

In some embodiments, the macromolecule is formulated in a composition. Suitable dosage forms include gels, ointments, pessaries, tampons, foams, lotions and creams. In some embodiments, the macromolecule is formulated in a gel as described above.

In some embodiments, the macromolecule or formulation of macromolecule is administered in multiple doses more than once per day, for example, twice per day (such as morning and night). In other embodiments, the dendrimer is administered in a single dose once per day, for example, at night.

In some embodiments, the macromolecule or formulation comprising the macromolecule is administered vaginally. In some embodiments, the dosage may be administered in a volume of 3.5-5 grams, especially 4-5 grams, more especially 5 grams, particularly when administered at night or immediately prior to the subject going to bed. The non-ambulating and predominantly horizontal position assumed during sleep assists in retention of the macromolecule formulation in the vagina increasing exposure time.

In some embodiments, the dosing occurs within proximity to sexual activity such as sexual intercourse, especially within 24 hours prior to or after intercourse, more especially within 3 hours prior to or after intercourse.

In some embodiments, the dosing occurs before, during or after menstruation, such as 1 to 3 days prior to anticipated onset of menstruation or within 24 hours of the end of menstruation and especially where dosing is administered for 2, 3, 4 or 5 days after the end of menstruation.

With current therapies, recurrence of BV is common, for example, because the original therapy was not completely effective or the subject is at high risk of reinfection.

In another aspect of the invention, there is provided a method of prophylaxis or reduction of recurrence of bacterial vaginosis in a subject, said method comprising administering to the subject an effective amount of a macromolecule comprising a polylysine, polyamidoamine, poly(etherhydroxylamine) or poly(propyleneimine) dendrimer of 1 to 5 generations and having one or more sulfonic acid-containing moieties attached to one or more surface amino groups of the outermost generation of the dendrimer, wherein said effective amount is administered 1 to 7 times per week.

The term "prophylaxis or reduction of recurrence" includes where the frequency of recurrence of BV is reduced and/or where the severity of BV infection in a recurrent episode is reduced or where recurrence of BV infection is prevented from occurring.

Severity of a BV infection may be determined by identification of one or more symptoms or diagnostic criteria associated with BV. Reduction of severity of BV infection includes where one or more of the symptoms or diagnostic criteria present in an earlier BV episode is not present, or present at a reduced level in the recurrent episode of BV. More preferably, recurrence frequency may be reduced to an occurrence of BV less frequently than once per year, once in 24 weeks, once in 16 weeks, once in 90 days, or once in 30 days.

In some embodiments, the administration of the macromolecule inhibits or kills microbes which are associated with BV, preferably anaerobic bacteria, and preferably Gram negative anaerobic bacteria. Microbes associated with BV include *Gardnerella vaginalis, Mobiluncus* spp., *M. curtisii, Atopobium vaginae, Prevotella* spp., *P. bivia, Bacteroides* spp., and *B. Ovatis*. Other microbes associated with BV are *Mycoplasma*, especially *M. hominus, Peptostreptococcus* ssp, and *coccobacillus* ssp. Most preferably *Gardnerella vaginalis* is killed or inhibited. In a some embodiments, the microbes associated with BV are inhibited, killed or prevented from colonizing the vaginal mucosa, whereas vaginal flora associated with a normal healthy vaginal environment are not significantly inhibited, or killed. The relationship between BV associated microbes and lactobacilli is reflected in the Nugent score.

In some embodiments normal Gram positive vaginal flora, and particularly lactic acid or hydrogen peroxide producing bacteria, are not significantly inhibited, or killed by the administration of the macromolecule. In particular, *Lactobacillus* ssp, especially *L. acidophilus, L. casei, L. plantarum, L. gasseri, L. jensenii* and *L. crispatus*, are not significantly inhibited or killed by administration of the macromolecule. More preferably *Lactobacillus* ssp. are not significantly inhibited or killed at concentrations equal to or less than 10 mg/mL (see Table 1).

In some embodiments, the effective amount is administered 2 to 3 times per week, for example, every third day. In other embodiments, the effective amount is administered 3 to 4 times a week, for example, on alternate days. In some embodiments, the effective amount is administered every day. In particular embodiments, the prophylactic or reducing therapy is continued for a prolonged period, such as months or years, for example, up to 25 years, such as for 1, 5, 10, 15 or 20 years. In other embodiments, the therapy is continued for 1 to 6 months, especially 2 to 5 months or 3 to 4 months, especially about 4 months or 16 weeks.

In some embodiments, the effective amount is in the range of 0.1 to 1000 mg per dose, including 0.1 to 500 mg per dose, 0.1 to 400 mg per dose, 0.1 to 300 mg per dose, 0.5 to 300 mg per dose, 0.5 to 200 mg per dose, 1 to 200 mg per dose, 2.5 to 200 mg per dose, 5 to 200 mg per dose, 10 to 200 mg per dose, 15 to 200 mg per dose, especially 30 to 200 mg per dose, 40 to 160 mg per dose, 40 to 150 mg per dose, 40 to 120 mg per dose, especially dosages such as about 50 mg per dose, 105 mg per dose and 150 mg per dose.

In some embodiments, particularly where therapy is continued for a prolonged period, the effective amount may be at the lower end of the effective range of doses. For example, when therapy is continued for a period of months or years, the effective amount may be in the range of 0.1 to 200 mg per dose, especially 0.1 to 100 mg per dose, 0.1 to 50 mg per dose, 0.1 to 25 mg per dose or 0.1 to 15 mg per dose.

In some embodiments, administration is in a single dosage. In some embodiments, administration is vaginal administration. Suitable dosage compositions are gels, ointments, tampons, pessaries, foams, creams and lotions, especially gels such as formulations of gels described above.

In some embodiments, the macromolecule or formulation comprising the macromolecule is administered vaginally. In some embodiments, the dosage may be administered in a volume of 3.5-5 grams, especially 4-5 grams, more especially 5 grams, particularly when administered at night or immediately prior to the subject going to bed. The non-ambulating and predominantly horizontal position assumed during sleep assists in retention of the macromolecule formulation in the vagina increasing exposure time.

In some embodiments, the dosing occurs within proximity to sexual activity such as sexual intercourse, especially within 24 hours prior to or after intercourse, more especially within 3 hours prior to or after intercourse. Such dosing is advantageous where a sexual partner is or is suspected to be the source of reinfection in recurrent BV.

In some embodiments, the dosing occurs before, during or after menstruation, especially within 24 hours of the end of menstruation and more especially dosing is administered for 2, 3, 4 or 5 days after the end of menstruation. Dosing may also occur 1 to 3 days prior to anticipated onset of menstruation. Such dosing is advantageous as menstruation is associated with recurrence of BV.

In a further aspect there is provided a method of reducing the incidence of fungal infection or other microbial infection in a subject during treatment of BV comprising treating the BV by administering to the subject an effective amount of a macromolecule comprising a polylysine, polyamidoamine, poly(etherhydroxylamine) or poly(propyleneimine) dendrimer of 1 to 5 generations and one or more sulfonic acid-containing moieties attached to one or more surface amino groups of the outermost generation of the dendrimer.

Many current treatments for BV include administration of antibiotics such as metronidazole, clindomycin and tinidazole. These treatments are often unable to distinguish between the infecting microbes (sometimes known as opportunistic microbes) and the bacteria normally present in healthy vaginal flora, and result in a reduction in normal flora. This reduction in normal flora allows other infecting microbes such as fungi or other microbes such as sexually transmitted microbes and gastrointestinal microbes to flourish resulting in increased susceptibility to fungal infections or microbial infection such as sexually transmitted diseases.

In some embodiments, the fungus is *Candida* spp. such as *Candida albicans* (Thrush), *C. tropicalis* and *C. glabrata* or *Trichophyton rubrum, Trichophyton mentagrophytes* and *Epidermophyton floccosum*, especially *C. albicans*. In other embodiments, the sexually transmitted microbial infection is human immunodeficiency virus (HIV), human papilloma virus (HPV), herpes simplex virus (HSV), *Molluscum conta-* giosum, *Neisseria gonorrhoeae* (Gonorrhea), *Chlamydia trachomatis* (Chlamydia), *Trichomonas vaginalis*, chancroid (*Haemophilus ducreyi*), *Klebsiella granulomatis* (granuloma inguianale) or *Treponema pallidum* (Syphilis). In yet other embodiments, the microbial infection may be derived from gastrointestinal flora such as *Escherichia* spp. such as *E. Coli*, *Clostridial* spp. such as *C. difficile, Fusobacterial* spp., *Saccharomyces* spp. and *Asperigillus* spp. In yet other embodiments, the microbial infection may be caused by *Staphylococcus aureus*.

In some embodiments, the effective amount is in the range of 15 to 1000 mg of macromolecule per day, especially 15 to 500 mg per day, 15 to 400 mg per day, 15 to 300 mg per day, 15 to 200 mg per day, 15 to 150 mg per day, 30 to 110 mg per day, 40 to 100 mg per day, 40 to 90 mg per day, 40 to 80 mg per day, 40 to 70 mg per day, more especially 40 to 60 mg per day, and most especially about 50 mg per day.

In some embodiments, the macromolecule or formulation of macromolecule is administered in multiple doses more than once per day, for example, twice per day (e.g., morning and night). In other embodiments, the macromolecule or formulation of macromolecule is administered in a single dose once per day, for example, at night. In some embodiments, the macromolecule or formulation of macromolecule is administered vaginally. Suitable dosage compositions include gels, ointments, pessaries, tampons, foams, creams and lotions, especially gels such as those described above.

The dendrimers useful in the invention are polylysine, polyamidoamine (PAMAM), poly(etherhydroxylamine) or poly(propyleneimide) (PPI) dendrimers having 1 to 5 generations. The macromolecule also comprises one or more sulfonic acid-containing moieties attached to the one or more surface amino groups of the outermost generation of the dendrimer.

Dendrimers are branched polymeric macromolecules composed of multiple branched monomers radiating from a central core moiety. The number of branch points increases upon moving from the dendrimer core to its surface and is defined by successive layers or "generations" of monomer (or building) units. Each generation of building units is numbered to indicate the distance from the core. For example, Generation 1 (G1) is the layer of building units attached to the core, Generation 2 (G2) is the layer of building units attached to Generation 1, Generation 3 (G3) is the layer of building units attached to Generation 2, Generation 4 (G4) is the layer of building units attached to Generation 3, Generation 5 (G5) is the layer of building units attached to Generation 4.

The outermost generation of building units provides the surface of the dendrimer and presents functional groups, in the present case amino groups, to which the at least one sulfonic acid-containing moiety is covalently bonded. The sulfonic acid-containing group may be directly bonded to the surface amino functional group or may be attached to the surface amino functional group through a linker.

The dendrimers comprise a single type of monomer unit (also referred to herein as a building unit). Each "branch" extending from the core of the dendrimer molecule has at least one layer or generation of building units. As used herein, the term "branch" refers to at least one generation of building units that is attached to one functional group on the core. In certain embodiments, each or any branch may have at least two layers or generations of building units. In further embodiments, each or any branch may have at least three or four layers or generations of building units. In yet further embodiments, each or any branch may independently have five layers or generations of building units.

The dendrimers contemplated herein can be prepared by methods known in the art and may be prepared in either a convergent manner (where, effectively, the branches are preformed and then attached to the core) or a divergent manner (where the layers or generations are successively built outwards from the core). Both these methods would be well understood to the skilled person.

The dendrimers may be composed of any suitable core and polylysine, polyamidoamine, poly(etherhydroxylamine) or poly(propyleneimine) monomer or building units.

As used herein, "core" refers to the moiety upon which successive layers or generations of monomers or building units are built (either through a divergent process or a convergent process), and may be any moiety having at least one reactive or functional site from which successive layers of monomer or building units are generated (or to which a preformed "branch" is attached). Some exemplary suitable cores contemplated herein include those having 1, 2, 3 or 4 reactive groups independently selected from, amino, carboxyl, thiol, alkyl, alkynyl, nitrile, halo, azido, hydroxylamine, carbonyl, maleimide, acrylate or hydroxy groups to which the layers or generations of building units or monomers can be attached. A core moiety may be the same as a building unit or may be different.

Exemplary cores include polyaminohydrocarbons, disulfide containing polyamines, poly(glycidyl ethers), aminoethanol, ammonia, arylmethylhalides, piperazine, aminoethylpiperazine, poly(ethyleneimine), alkylene/arylene dithiols, 4,4-dithiobutyric acid, mercaptoakylamines, thioether alkylamines, isocyanurate, heterocycles, macrocycles, polyglycidylmethacrylate, phosphine, porphines, oxiranes, thioranes, oxetanes, aziridines, azetidines, multiazidofunctionalities, siloxanes, oxazolines, carbamates or caprolactones.

Some non-limiting examples of core moieties contemplated herein include diamino $C_2$-$C_{12}$ alkanes such as ethylene diamine, 1,4-diaminobutane and 1,6-diaminohexane. However, it will be appreciated that the core is not necessarily a linear moiety with a single reactive group at each end. Non-linear, cyclic or branched core moieties are also contemplated by the present invention. For example, arylmethylamines such as benzhydrylamine (BHA), are suitable cores.

The building units of the dendrimer are lysine building units:

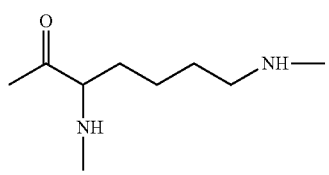

Amidoamine building units:

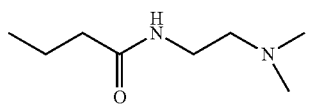

Etherhydroxyamine building units:

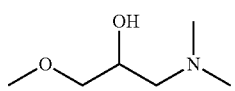

or propyleneimine building units:

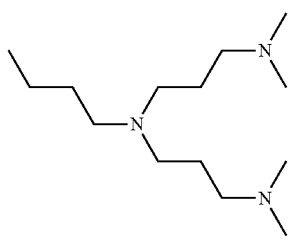 [SMILES: CCCCN(CCCN(C)C)CCCN(C)C]

In a particular embodiment, the dendrimer is a polylysine dendrimer, especially a polylysine dendrimer with a benzhydrylamine core.

The sulfonic acid-containing moiety is any moiety that is able to present the sulfonic acid group on the surface of the dendrimer. In some embodiments, the sulfonic acid-containing moiety has one sulfonic acid group. In other embodiments, the sulfonic acid-containing moiety has more than one sulfonic acid group, for example 2 or 3 sulfonic acid groups, especially 2 sulfonic acid groups. In some embodiments, the sulfonic acid-containing moiety comprises an aryl group, such as a phenyl group or naphthyl group, especially a naphthyl group.

Examples of suitable sulfonic acid-containing moieties include but are not limited to:

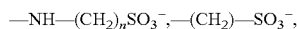

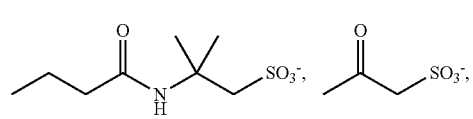

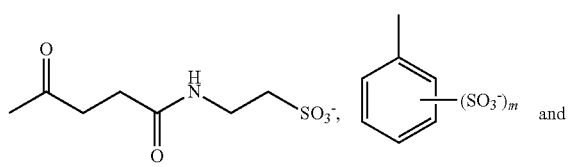

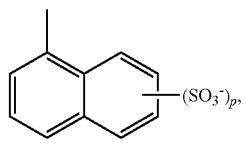

in which n is 0 or an integer of 1 to 20, m is an integer of 1 or 2 and p is an integer of 1 to 3.

In some embodiments, the sulfonic acid-containing moiety is selected from:

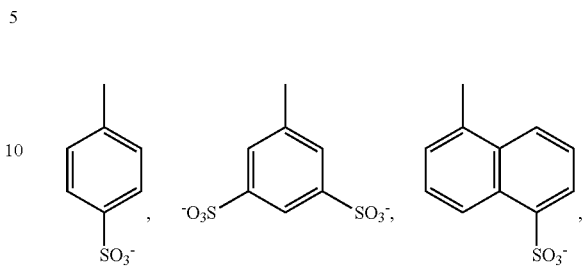

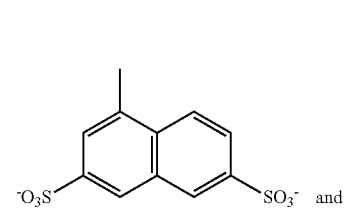, especially

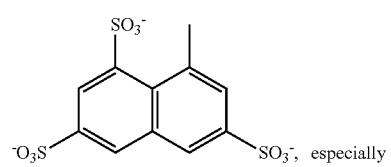

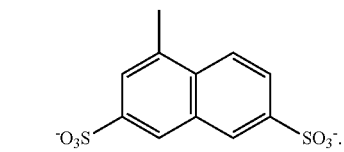.

In some embodiments, the sulfonic acid-containing moiety is directly bonded to the surface amino group of the dendrimer. In other embodiments, the sulfonic acid-containing moiety is attached to the surface amino group of the dendrimer through a linker group.

Suitable linker groups include alkylene or alkenylene groups in which one or more non-adjacent carbon atoms is optionally replaced by an oxygen or sulfur atom to provide an ether, thioether, polyether or polythioether; or a group —$X_1$—$(CH_2)_q$—$X_2$ wherein $X_1$ and $X_2$ are independently selected from —NH—, —C(O)—, —O—, —S— and —C(S), and q is 0 or an integer from 1 to 10, and in which one or more non-adjacent ($CH_2$) groups may be replaced with —O— or —S— to form an ether, thioether, polyether or polythioether.

In a particular embodiment, the linker is

-O—$CH_2$—C(O)—* in which # designates attachment to the sulfonic acid-containing moiety and * designates attachment to the surface amino group of the dendrimer.

Exemplary dendrimers useful in the invention include formulae I (SPL-7013), II (SPL-7320) and III (SPL-7304):
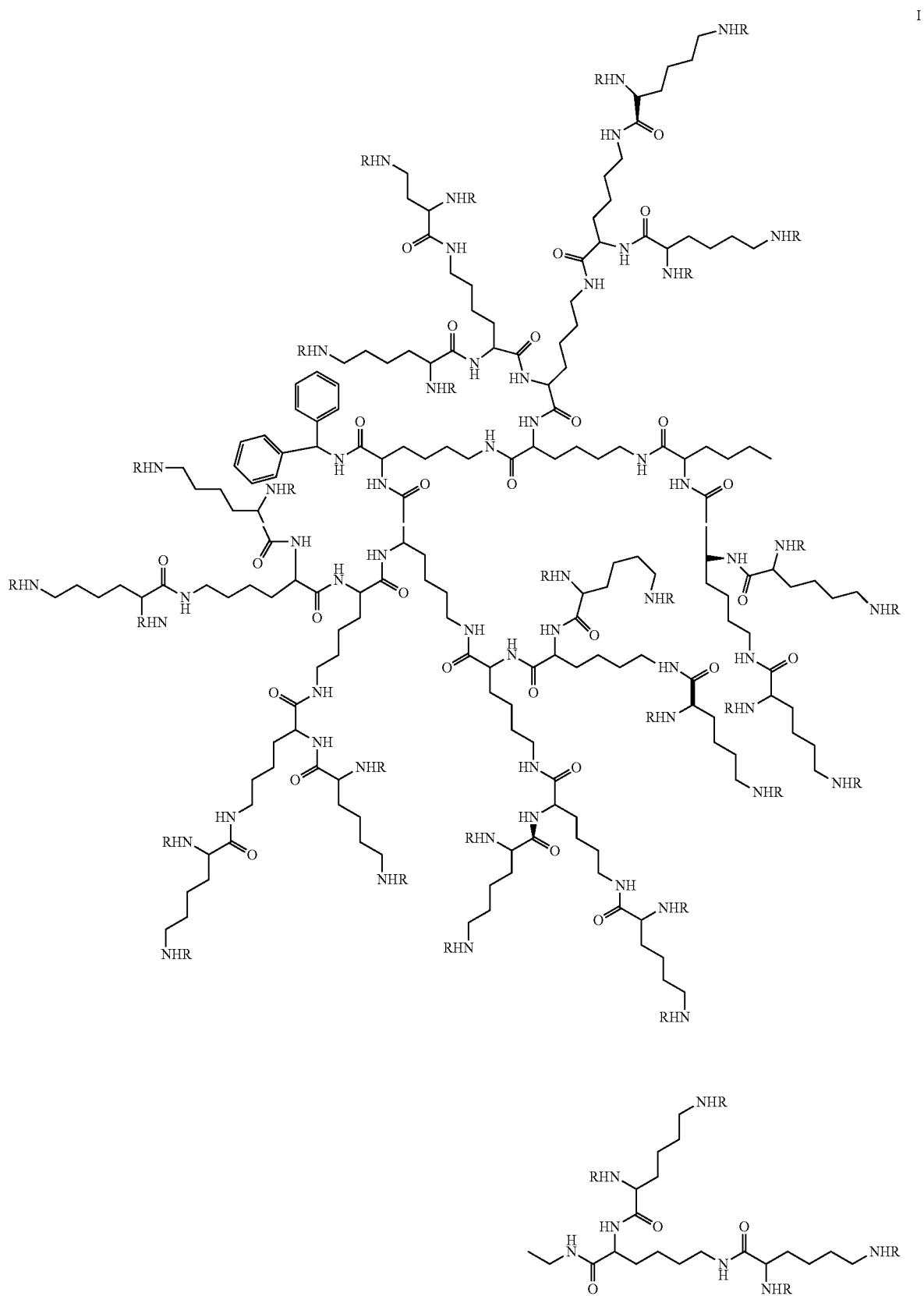
I

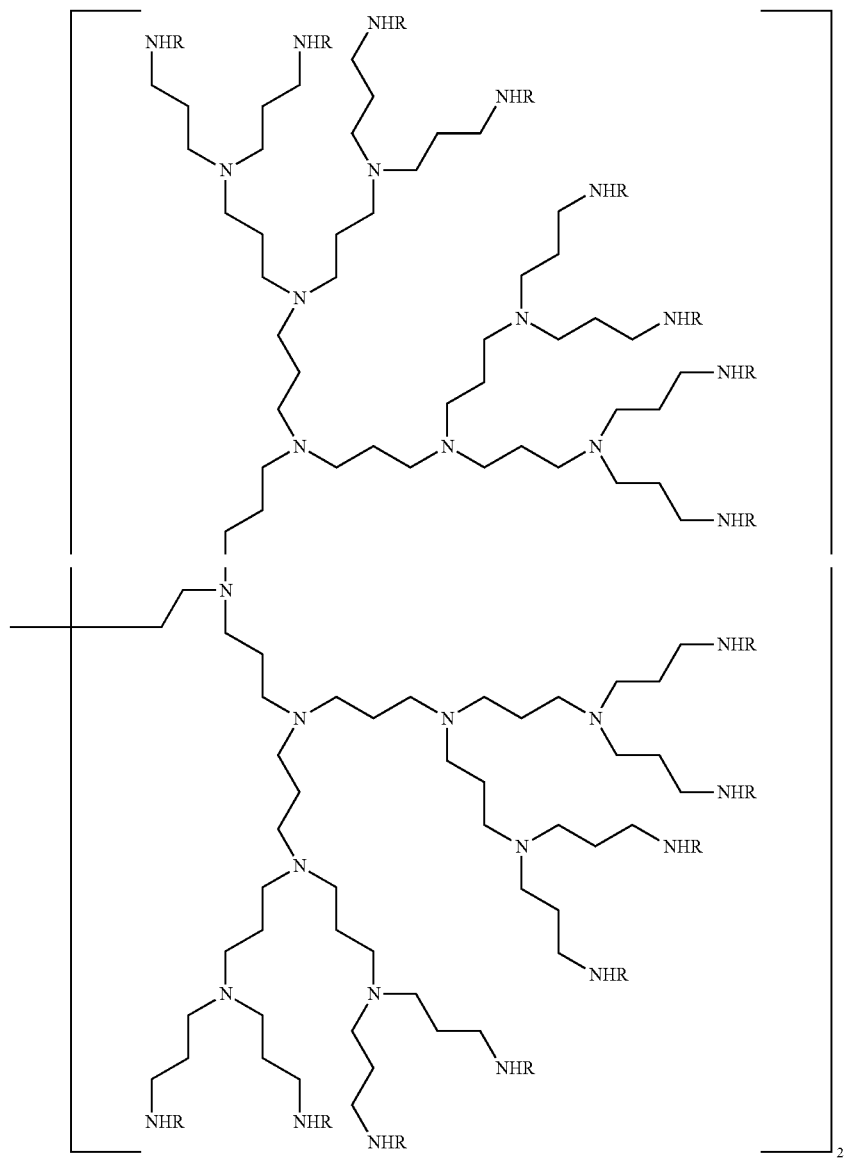
II

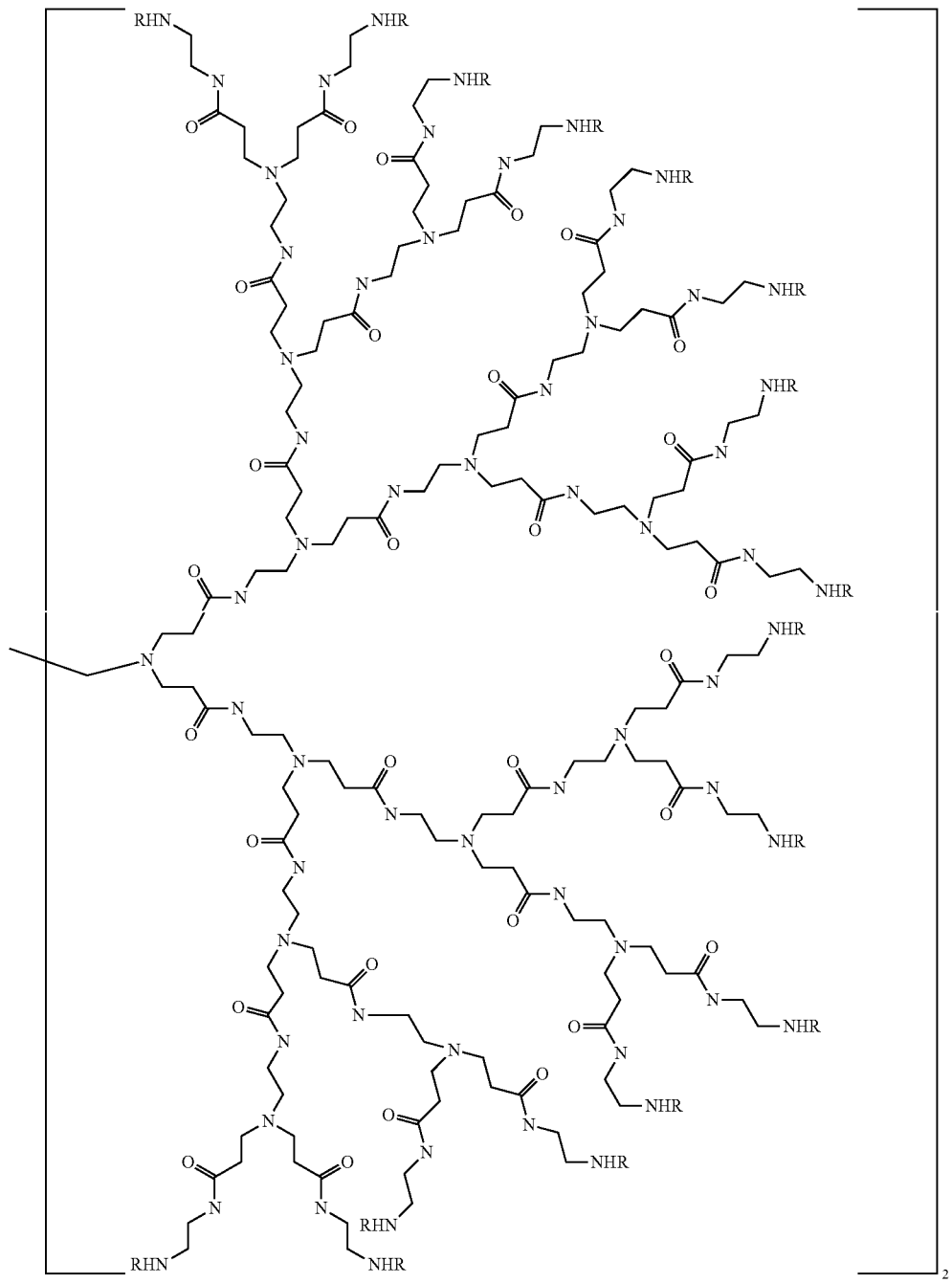

in which the R group is represented by:

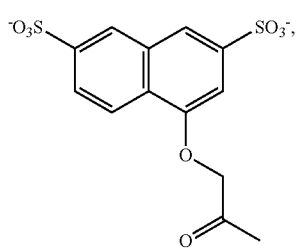

or a pharmaceutically acceptable salt thereof.

The synthesis of Formulae I, II and III is described in WO 02/079299.

Suitable pharmaceutically acceptable base addition salts include, but are not limited to, metallic salts such as the aluminium, calcium, lithium, magnesium, potassium, sodium and zinc salts, as well as organic salts made from organic amines such as N,N'-dibenzyl-ethylenediamine, chloroprocaine, diethanolamine, ethylenediamine, dicyclohexylamine, meglumine (N-methylglucamine) and procaine, quaternary amines such as choline, and sulphonium and phosphonium salts.

The present invention will now be more fully described with reference to the accompanying examples. It should be understood, however, that the description following is illustrative only and should not be taken in any way as a restriction on the generality of the invention described above.

EXAMPLES

Example 1

Selectivity of Formula I in Anaerobes

Test Articles

The test articles (Formula I, also referred to as SPL-7013, powder and gel placebo) were stored at ambient conditions until assayed.

Assays were conducted targeting test concentration of SPL-7013 powder of 1, 5, 10 and 30 mg/mL. For these assays, the SPL-7013 powder was dissolved and diluted in de-ionized water to achieve the final targeted concentrations in the various agar media.

The comparator drug, Imipenem was obtained from the United States Pharmacopeia (cat. #1337809, Lat # HOE040) and stored at −20° C. in buffer at pH 7.2 and a stock concentration of 320 µg/mL.

Organisms

Test organisms for the assays were recent clinical isolates or reference strains acquired from the American Type Culture Collection (ATCC; Manassas, Va.). The quality control organism included in the assay was *Bacteroides fragilis* 0123 (ATCC 25285).

The growth and test media were those recommended by the Clinical Laboratory Standards Institute (CLSI; 1, 2, 3) for growth and susceptibility testing of anaerobes. The test organisms were maintained frozen at −80° C. The isolates were sub-cultured on Supplemented *Brucella* Agar (SBA) plates (Teknova, Hollister, Calif.) for the anaerobes. The anaerobic bacteria were incubated in a Bactron II anaerobic chamber at 35° C. for 48 hours (atmosphere of 5% hydrogen, 5% carbon dioxide, 90% nitrogen).

Test Media

The medium employed for the anaerobic agar dilution MIC assay was *Brucella* Agar (Becton Dickinson, Sparks, Md. #211086, Lot #7166673) supplemented with hemin (Strem Chemicals, Lot #07.0830), Vitamin K$_1$ (Pfaltz and Bauer, Lot #9799), and lysed sheep blood (Cleveland Scientific, Lot # S03582). All media was prepared according to Clinical and Laboratory Standards Institute (CLSI) guidelines (1, 2, 3). For the broth microdilution assay, the medium was prepared at 105% normal weight to offset the 5% drug solution volume (10 µL drug solution) in the final microdilution panels/agar plates.

Agar Dilution Minimal Inhibitory Concentration (MIC) Assay Procedure (Anaerobes)

Anaerobic bacteria were assayed using a reference agar dilution method previously described (NCCLS. *Methods for Antimicrobial Susceptibility Testing of Anaerobic Bacteria; Approved Standard*—Sixth Edition. NCCLS document M11-A6 [ISBN 1-56238-517-8]. NCCLS, 940 West Valley Road, Suite 1400, Wayne, Pa. 19087-1898 USA, 2004). Drug dilutions and drug-supplemented agar plates were prepared manually. Following inoculation, the drug-supplemental plates were incubated at 35° C. for 48 hours in the anaerobic environment of the Bactron II. The MIC was read per CLSI guidelines (NCCLS referred to above).

MIC data from susceptibility testing in which SPL-7013 powder was tested at concentrations of 1, 5, or 30 mg/mL is shown in Table 1. Table 1 shows that there were a few anaerobic pathogens that were sensitive to either 30 mg/mL (*B. ovatus, P. bivia*), 10 mg/mL (*L. crispatus*), or 5 mg/mL (*G. vaginalis*) of SPL-7013.

TABLE 1

| Organism | Micromyx Number | SPL7013 Powder (mg/mL) | Imipenem (µg/mL) |
|---|---|---|---|
| *Mobiluncus curtisii* | 4145 | >30 | ≤0.03 |
| *Mobiluncus mulieris* | 4146 | >30 | ≤0.03 |
| *Lactobacillus acidophilus* | 0681 | >30 | 0.12 |
| *Lactobacillus casei* | 1722 | >30 | 0.5 |
| *Lactobacillus plantarum* | 2791 | >30 | 2 |
| *Lactobacillus crispatus* | 4147 | 10 | 0.12 |
| *Lactobacillus gasseri* | 4148 | >30 | 0.25 |
| *Lactobacillus jensenii* | 4149 | >30 | 0.25 |
| *Bacteroides fragilis* | 3374 | >30 | 2 |
| *B. fragilis* | 0123 | >30 | 0.12 |
| | | | QC Range (0.03-0.12)[1] |
| *Bacteroides ovatus* | 3503 | >30 | 0.25 |
| *B. ovatus* | 3508 | 30 | ≤0.03 |
| *Bacteroides ureolyticus* | 4150 | >30 | 0.25 |
| *Fusobacterium nucleatum* | 1269 | >30 | ≤0.03 |
| *Anaerococcus prevotii* | 4151 | >30 | 0.06 |
| *Anaerococcus tetradius* | 4152 | >30 | ≤0.03 |
| *Peptostreptococcus anaerobius* | 3526 | >30 | ≤0.03 |
| *Prevotella bivia* | 3447 | 30 | ≤0.03 |
| *Prevotella intermedia* | 3002 | >30 | ≤0.03 |
| *Prevotella melaninogenica* | 3005 | >30 | ≤0.03 |
| *Porphyromonas levii* | 3003 | >30 | 0.06 |
| *Porphyromonas asaccharolytica* | 3004 | >30 | ≤0.03 |
| *Gardnerella vaginalis* | 4153 | 5 | 0.12 |

[1]( ) Clinical and Laboratory Standards Institute Acceptable Limits for Quality Control Strains As can be seen from Table 1, *Gardnerella vaginalis*, a bacterium associated with BV, was sensitive to SPL-7013 at 5 mg/mL whereas many of the *Lactobacillus* species which are present in normal vaginal flora were not affected by SPL-7013 or affected at higher concentrations (*Lactobacillus crispatus*, 10 mg/mL).

Example 2

To assess the anti-microbial properties of a solution of aqueous SPL-7013, two aqueous solutions were prepared, one at 5% w/v, and the second at 28% w/v. Standard preservative effectiveness tests (according to USP <51> "Antimicrobial Effectiveness Test") were conducted in order to challenge the capacity of each solution to limit microbial growth over a one month period.

All samples were prepared in 250 mL HDPE screw-cap vials, and non-sterile.

5% w/w Solution
  A sample of SPL-7013 (7.5402 g) was dissolved in water (150 mL), with the sample agitated to facilitate dissolution. The resulting mixture had a concentration calculated as 5.0268% w/v.

28% w/w Solution
  A sample of SPL-7013 (42.0012 g) was dissolved in water (150 mL), with the sample agitated to facilitate dissolution. The resulting mixture had a concentration calculated as 28.0008% w/v.

Test Method

The SPL-7013 sample solutions were used as prepared, and tested according to USP <51> "Antimicrobial Effectiveness Test". In this, the solutions were challenged with 5 microbial organisms, and the population of each microorganism is monitored as a function of time.

The challenge microorganisms were as follows:
*Pseudomonas aeruginosa*, ATCC 9027
*Staphylococcus aureus*, ATCC 6538
*Candida albicans*, ATCC 10231
*Aspergillus niger*, ATCC 16404
*Escherichia coli*, ATCC 8739

Test inoculum is added to each sample such that the final concentration after inoculation is between $1 \times 10^5$ and $1 \times 10^6$ cfu per mL of product. The initial concentration of viable microorganisms in each test preparation is estimated based on the concentration of microorganisms in each of the standardized inoculum as determined by the plate-count method. The inoculated containers are incubated at $22.5 \pm 2.5°$ C. and sampled after 14 and 28 days. On sampling, the concentration of each microorganism is determined by the plate-count method. Changes in microorganism concentrations are expressed in terms of log reduction. No increase in microorganism concentration is defined as not more than a 0.5 log value than the previous measured.

Results and Discussion

TABLE 2

| | 5% w/v solution | | |
|---|---|---|---|
| | Initial Count/ | Final Count/cfu per g * | |
| Organism | cfu per g | 14 days | 28 days |
| P. aeruginosa | $1.0 \times 10^6$ | <10 | <10 |
| S. aureus | $8.6 \times 10^5$ | <10 | <10 |
| C. albicans | $1.3 \times 10^6$ | $6.6 \times 10^5$ | $4.5 \times 10^5$ |
| A. niger | $8.0 \times 10^5$ | $7.0 \times 10^5$ | $4.1 \times 10^5$ |
| E. Coli | $7.9 \times 10^5$ | 15 (est) | 25 (est) |

* < indicates 'less than', est indicates 'estimate'

As shown in Table 2, the 5% w/v solution of SPL-7013 acted as a bactericide against *Pseudomonas aeruginosa*, *Staphylococcus aureus* and *Escherichia coli* over a 14 day period, with no subsequent increase in microorganism concentration observed. The same test solution demonstrated a reduced bactericidal effect with respect to the *Candida albicans* and *Aspergillus niger* inoculums after 14 days, with gradual reduction in microorganism concentration (i.e. >0.5 log unit decrease) by the 28 day time point.

TABLE 3

| | 28% w/v solution | | |
|---|---|---|---|
| | Initial Count/ | Final Count/cfu per g * | |
| Organism | cfu per g | 14 days | 28 days |
| P. aeruginosa | $1.0 \times 10^6$ | <10 | <10 |
| S. aureus | $8.5 \times 10^5$ | <10 | <10 |
| C. albicans | $1.3 \times 10^6$ | $7.3 \times 10^4$ | 340 |
| A. niger | $8.0 \times 10^5$ | $1.0 \times 10^6$ | $8.9 \times 10^5$ |
| E. Coli | $7.9 \times 10^5$ | <10 | <10 |

* < indicates 'less than'

As shown in Table 3, the 28% w/v solution of SPL-7013 acted as a bactericide against *Pseudomonas aeruginosa*, *Staphylococcus aureus* and *Escherichia coli* over a 14 day period, and also against *Candida albicans* over 28 days. The same test solution prevented growth of the *Aspergillus niger* inoculum over the duration of the test.

The antibacterial properties of the two test solutions (5% and 28% w/v SPL-7013 in water) as determined by the USP <51> "Antimicrobial Effectiveness Test" indicate that both meet the pass criteria of the test for topical preparations.

Example 3

A clinical study was carried out in which 66 women with clinically diagnosed BV were randomized into four groups.
1. 5 g 3% SPL-7013 gel each night for 7 nights
2. 5 g 1% SPL-7013 gel each night for 7 nights
3. 5 g 0.5% SPL-7013 gel each night for 7 nights
4. 5 g HEC Placebo gel each night for 7 nights The criteria for inclusion in the study were women 18-45 years of age, with a clinical diagnosis of BV according to Amsel's criteria and a Nugent Score of ≥4. The subjects were otherwise healthy. Subjects were excluded if they had sexually transmitted infections.

Each subject was assessed at day 9-12 from start of treatment (End of Treatment, EOT) and again between day 21-30 (Test of Cure, TOC).

Each subject was assessed for Clinical Cure, Nugent Cure, Therapeutic Cure and Therapeutic Resolution at both EOT and TOC. The results are shown in Table 4.

Further results of the trial in additional participants using the same clinical study protocol are shown in Table 5.

TABLE 4

| | EOT (%) | | | | | TOC (%) | | | | |
|---|---|---|---|---|---|---|---|---|---|---|
| Endpoint | 3% SPL7013 | 1% SPL7013 | 0.5% SPL7013 | Any SPL7013 | HEC Placebo | 3% SPL7013 | 1% SPL7013 | 0.5% SPL7013 | Any SPL7013 | HEC Placebo |
| Clinical Cure (No discharge and ≤1 other Amsel) | 50 | 83.3 | 57.1 | 62.2 | 11.1 | 8.3 | 54.6 | 21.4 | 27 | 10.0 |
| Nugent Cure (Nugent score ≤3) | 25 | 33.4 | 14.2 | 23.7 | 0 | 0 | 27.3 | 10 | 13 | 0 |
| Therapeutic Cure (Both Clinical and Nugent Cures) | 0 | 25 | 14.3 | 13.2 | 0 | 0 | 27.3 | 7.7 | 11.1 | 0 |
| White to Grey Homogenous Discharge (Present at Baseline to Absent) | 81.8 | 100 | 85.7 | 89.2 | 37.5 | 20 | 63.6 | 45.5 | 43.8 | 28.6 |
| Whiff Test (Present at Baseline to Absent) | 63.6 | 91.7 | 57.1 | 70.3 | 12.5 | 20 | 63.6 | 54.5 | 46.9 | 28.6 |
| Vaginal pH > 4.5 (Present at Baseline to Absent) | 54.5 | 50 | 28.6 | 43.2 | 0 | 10 | 50 | 18.2 | 25.8 | 14.3 |

TABLE 4-continued

|  |  | EOT (%) | | | | | TOC (%) | | | | |
| --- | --- | --- | --- | --- | --- | --- | --- | --- | --- | --- | --- |
| Endpoint | | 3% SPL7013 | 1% SPL7013 | 0.5% SPL7013 | Any SPL7013 | HEC Placebo | 3% SPL7013 | 1% SPL7013 | 0.5% SPL7013 | Any SPL7013 | HEC Placebo |
| Clue Cells (Present at Baseline to Absent) | | 63.6 | 91.7 | 64.3 | 73 | 12.5 | 20 | 72.7 | 27.3 | 40.6 | 14.3 |
| Nugent Score | ≥7 to ≤3[1] | 25 | 16.7 | 7.1 | 15.8 | 0 | 0 | 9.1 | 10 | 6.5 | 0 |
|  | ≥7 to 4-6[2] | 50 | 50 | 28.6 | 42.1 | 0 | 10 | 18.2 | 0 | 9.7 | 14.3 |
|  | ≥7 to ≥7[3] | 0 | 16.7 | 21.4 | 13.2 | 100 | 70 | 45.5 | 50 | 54.8 | 85.7 |
|  | ≥4 to ≤3[4] | 25 | 33.4 | 14.2 | 23.7 | 0 | 0 | 27.3 | 10 | 13 | 0 |
|  | ≥7 to 0-6 | 75 | 66.7 | 35.7 | 57.9 | 0 | 10 | 27.3 | 10 | 16.2 | 14.3 |
| No Abnormal Discharge | Investigator | 50 | 75 | 71.4 | 65.8 | 22.2 | 16.7 | 63.6 | 42.9 | 40.5 | 50 |
|  | Subject | 69.2 | 91.7 | 75 | 78.4 | 42.9 | 50 | 72.7 | 61.5 | 61.1 | 30 |
| No Unpleasant Odor | Investigator | 66.7 | 100 | 71.4 | 78.9 | 22.2 | 41.7 | 72.7 | 64.3 | 59.5 | 50 |
|  | Subject | 76.9 | 91.7 | 84.6 | 84.2 | 42.9 | 50 | 63.6 | 69.2 | 61.1 | 66.7 |

[1] = BV to Normal;
[2] = BV to intermediate;
[3] = BV to BV;
[4] = abnormal to normal.

The results in Table 4 show that a Clinical Cure was achieved at EOT in 62.2% of subjects treated with SPL-7013 gel, and 27% of subjects treated with SPL-7013 at TOC. Surprisingly the 1% SPL-7013 gel formulation performed significantly better at EOT (83% Clinical Cure) and TOC (55% Clinical Cure) than other SPL-7013 formulations.

The results in Table 4 show that Nugent Score was reduced to normal at the EOT in about 25% of subjects treated with 3% SPL-7013 gel, about 33% of subjects treated with 1% SPL-7013 gel and 14% in subjects treated with 0.5% SPL-7013 gel. Nugent Score was reduced to normal at the TOC in 0% of subjects treated with 3% SPL-7013 gel, 27% of subjects treated with 1% SPL-7013 gel and about 10% of subjects treated with 0.5% SPL-7013 gel.

The results in Table 4 show that the Therapeutic Cure at EOT was about 25% and at TOC was 27% of subjects treated with 1% SPL-7013 gel. This is a higher cure rate than seen with other doses of SPL-7013 gel. Therapeutic Cure for the placebo groups at EOT and TOC was 0%.

Equally, Table 4 shows that the 1% SPL-7013 gel performed better in relation to resolution of the Amsel's criteria also. At EOT, resolution of vaginal discharge was 100%, whiff test was 92%, vaginal pH was 50% and clue cells was 92% with 1% SPL-7013 gel compared to 82%, 64%, 55% and 64% respectively for 3% SPL-7013 gel and 86%, 57%, 29% and 64% respectively for 0.5% SPL-7013 gel. At TOC, resolution of vaginal discharge was 64%, whiff test was 64%, vaginal pH was 50% and clue cells 73% for 1% SPL-7013 gel compared to 20%, 20%, 10% and 20% respectively for 3% SPL-7013 gel and 46%, 55%, 18% and 27% respectively for 0.5% SPL-7013 gel.

During the study no participants who received SPL-7013 gel and two participants receiving the HEC placebo gel experienced a severe adverse event (AE) during treatment. Only one participant experienced a serious AE, but this was prior to administration of any study product. These data indicate a very low level of AEs in this study.

TABLE 5

|  | EOT (%) | | | | | TOC (%) | | | | |
| --- | --- | --- | --- | --- | --- | --- | --- | --- | --- | --- |
| Endpoint | 3% SPL7013 | 1% SPL7013 | 0.5% SPL7013 | Any SPL7013 | HEC Placebo | 3% SPL7013 | 1% SPL7013 | 0.5% SPL7013 | Any SPL7013 | HEC Placebo |
| Clinical Cure (No discharge and ≤1 other Amsel) | 62.5 | 74.1 | 55.2 | 63.8 | 22.2 | 28.0 | 46.2 | 23.3 | 32.1 | 11.5 |
| Therapeutic Cure (Both Clinical and Nugent Cures) | 8.3 | 26.9 | 17.2 | 17.7 | 7.4 | 16.0 | 19.2 | 10.0 | 14.8 | 7.7 |
| Therapeutic Resolution (Clinical Cure and Nugent Score <6) | 54.2 | 50.0 | 37.9 | 46.8 | 11.1 | 20.0 | 34.6 | 10.0 | 21.0 | 11.5 |
| Nugent Score ≥7 to ≤3* | 30.0 | 21.7 | 28.6 | 26.6 | 0 | 15.0 | 21.7 | 13.6 | 16.9 | 4.2 |

* = BV to Normal.

These results are consistent with the data presented in Table 4 above in that the 1% formulation performs better in the treatment of BV at EOT and TOC.

Example 4

Clinical Study for Prophylaxis of Recurrence of BV

A double blind, multi-centre, randomized, placebo controlled, dose-ranging study to determine the safety and efficacy of SPL-7013 gel administered vaginally for the prophylaxis of recurrence of BV is planned.

The trial will assess clinical efficacy of two dose levels, chosen from 0.5%, 1% and 3% SPL-7013 gel compared to placebo gel and will determine microbiological and overall efficacy of two dose levels, chosen from 0.5%, 1% and 3% SPL-7013 gel, determine safety and tolerability and determine patient perceived symptom resolution.

Primary Endpoint

The primary end point will be the presence or absence of BV at the end of 16 weeks' use of SPL-7013 gel.

Secondary Endpoints
    Presence or absence of BV at the 8-week follow-up visit (Week 24).
    Time to recurrence of BV from the end of the initial metronidazole treatment.
    Presence or absence of individual criteria of BV, including subject reported symptoms, Amsel's criteria, Nugent Score criteria, and BV Blue® test results.
    Treatment acceptability assessed using the Treatment Satisfaction Questionnaire for Medication (TSQM).
    Incidence of non-BV vaginal infections.
    Safety endpoints will include the incidence of AEs and ordinal ratings of signs and symptoms of genital irritation.

Study Population
    Female subjects aged 18-45 years inclusive with a current episode of BV and a history of recurrent BV (defined as at least 3 documented episodes in the previous 12 months, including the current episode).

Duration/Participant
    Total duration of approx. 26 weeks comprising: up to a 1 week Screening period; a 7 day open label period of treatment with Metronidazole ("Acute Treatment Phase"); a 16 week period of treatment with SPL-7013 Gel or HEC placebo gel ("Double-Blind Treatment Phase") and an 8 week Follow-Up Period ("Follow-Up Phase").

Study Procedures
    Following provision of written informed consent and a maximum 1 week Screening period, eligible Participants will receive a 7 day course of Metronidazole administered orally (500 mg BD). Participants will then have an assessment of their BV at Day 4+/−1 day after completion of open label treatment with Metronidazole.
    Women found to have responded to treatment (resolution defined as no clinical symptoms (asymptomatic) and no more than 2 of 4 Amsel's criteria) and who meet the Part 2 Inclusion and Exclusion criteria will be eligible to enter the Double-Blind Treatment Phase. Eligible Participants will be randomized in a ratio of 1:1:1 to receive two dose levels, chosen from 0.5%, 1% and 3% SPL-7013 gel or HEC placebo gel at a dose of 5 g administered vaginally at night (prior to bed) on every second day for 16 consecutive weeks.
    During the 16-week Double-Blind Treatment Phase, Participants will visit the clinic every 4 weeks. At the end of Week 16, the End of Treatment (EDT) Visit will be conducted. Participants will then continue into the Follow-Up Phase, during which clinic visits will be conducted at Weeks 20 and 24.
    Details of procedures to be conducted at the study visits are presented in Table 6 Schedule of Study Assessments and Procedures.
    Study Participants who do not respond to the one week Metronidazole treatment regimen (as per the protocol definition) will be designated as a "Metronidazole Non-Responder" and will be discontinued from further study assessments.
    Participants who experience a recurrence of BV (as per the protocol definition) during or after the Double-Blind Treatment Phase (i.e., Between Visit 1 (Baseline)) will be offered rescue therapy which should only include orally administered antibiotics (e.g., Metronidazole, Clindamycin) in line with local practice. Participants who receive rescue therapy will cease further treatment with study drug, will complete the early termination visit procedures, and will be discontinued from the study.

Safety Parameters
    Adverse events and signs and symptoms of genital irritation observed by or reported to the investigator or noted on the subject diary cards will be evaluated. The incidence of non-BV vaginal infections, concomitant medication use, and compliance with the treatment regimen will also be assessed. Additional safety parameters will include urinalysis, physical and pelvic/gynecological examination, medical & sexual history, vital signs, urinary pregnancy test and symptom assessment.

Statistical Analyses
    Primary analysis will be a comparison of the two chosen SPL-7013 gel doses (from 0.5% or 1% or 3%) vs. HEC placebo gel.
    Assuming that the proportion of women who do not relapse by the Week 16 visit is between 65-70% for SPL-7013 gel and is 40% for HEC placebo gel, a sample size of a minimum of 54 evaluable subjects per treatment arm will provide 80% power to detect a treatment difference with an alpha significance level of 0.05.
    Both scenarios assume a Metronidazole treatment failure rate of 12%, and a participant drop-out rate at 4 months of 12%.

TABLE 6

Schedule of Study Assessments and Procedures

| Examination | Screening Visit 1 Day −16 to Day −9 | Acute Treatment Phase Day −11 to Day −4 (±1 day) | Double-blind Treatment Phase | | | Follow-up Phase | |
|---|---|---|---|---|---|---|---|
| | | | Visit 2 Day 1 Baseline | Visits 3, 4, 5 Weeks 4, 8, 12 | Visit 6/ Withdrawal Week 16/ EOT | Visit 7 Week 20 | Visit 8 Week 24/ EOS |
| Informed consent | X | | | | | | |
| Demographic information | X | | | | | | |
| Medical history | X | | | | | | |
| Sexual history questionnaire | X | | | | | | |
| Prior & concomitant medications | X | | X | X | X | X | X |
| Inclusion/exclusion criteria[a] | X | | X | | | | |
| Vital signs | X | | | | | | |
| Physical examination[b] | X | | X | X | X | X | X |
| Urine pregnancy test | X | | X | | X | | |
| Urine dipstick test[c] | X | | X | | | | |
| Blood samples for HIV tests | X | | | | | | |
| Blood samples for HSV-2 test | | | X | | X | | |
| Pelvic examination | X | | X | X | X | X | X |
| Pap smear (Thin Prep ®), if needed[d] | X | | | | | | |
| Vaginal sample (Thin Prep ®) for potential HPV analysis | | | X | | X | | |

TABLE 6-continued

Schedule of Study Assessments and Procedures

| Examination | Screening Visit 1 Day −16 to Day −9 | Acute Treatment Phase Day −11 to Day −4 (±1 day) | Double-blind Treatment Phase | | | Follow-up Phase | |
|---|---|---|---|---|---|---|---|
| | | | Visit 2 Day 1 Baseline | Visits 3, 4, 5 Weeks 4, 8, 12 | Visit 6/ Withdrawal Week 16/ EOT | Visit 7 Week 20 | Visit 8 Week 24/ EOS |
| Vaginal sample for clue cells, candidiasis | X | | X | X | X | X | X |
| Vaginal sample for storage and potential analysis of vaginal microflora | X | | X | | X | X | |
| Vaginal sample for Nugent score (Gram stain) | X | | X | | X | | |
| Vaginal sample(s) for STI testing[e] | X | | X[e] | X[e] | X[e] | X[e] | X[e] |
| BVBlue ® test | X | | X | X | X | X | X |
| BV assessment (subject's symptoms reported & Amsel's Criteria[f]) | X | | X | X | X | X | X |
| Dispense metronidazole | X | | | | | | |
| Metronidazole therapy | | X | | | | | |
| Randomization | | | X | | | | |
| Dispense study medication | | | X | X | | | |
| Issue weekly diary cards | | | X | X | X | X | |
| Compliance | | | X | X | X | X | X |
| Adverse events | X | | X | X | X | X | X |
| Review and collect diary cards | | | | X | X | X | X |
| Collect drug applicators | | | | | X | X | |
| Acceptability Questionnaire | | | | | X | | |

EOT = end of treatment; EOS = end of study; BV = bacterial vaginosis; STI = sexually transmitted infection; HIV = human immunodeficiency virus; HSV-2 = herpes simplex virus type 2.
[a]Inclusion/exclusion criteria Part 1 and Part 2 will be used at Screening and Baseline, respectively.
[b]A physical examination will be performed only at the investigator's discretion to assess a stable, pre-existing condition or to assess/diagnose an emergent AE.
[c]Urinalysis by dipstick will be used for measurement of pH, glucose, protein, blood, bilirubin, ketones, urobilinogen, nitrites, leukocytes. If indicated by a dipstick result that is abnormal and in the investigator's opinion is clinically significant, chemistry, microscopy, culture and sensitivity may also be performed.
[d]Pap smear (Thin Prep ®) required if no recent results (≤2 years) are available.
[e]After Screening, samples for STI testing will be taken only if clinically indicated.
[f]Amsel's Criteria will be assessed on-site by the investigator.

What is claimed is:

1. A method of reduction of recurrence of bacterial vaginosis in a subject in need thereof, said method comprising administering to the subject an effective amount of a macromolecule comprising a polylysine, polyamidoamine, poly(etherhydroxylamine) or poly(propyleneimine) dendrimer of 1 to 5 generations and one or more sulfonic acid-containing moieties attached to one or more surface amino groups of the outermost generation of the dendrimer, wherein said effective amount is administered 1 to 7 times per week, thereby reducing recurrence of bacterial vaginosis in the subject.

2. The method according to claim 1 wherein the effective amount is 30 mg to 200 mg per dose.

3. The method according to claim 1 wherein the effective amount is 15 mg to 150 mg per dose.

4. The method according to claim 1 wherein administration is 3 to 4 times per week.

5. The method according to claim 1 wherein the macromolecule is administered in a gel formulation.

6. The method according to claim 1 wherein administration occurs within 24 hours prior to or after sexual activity.

7. The method according to claim 1 wherein administration occurs before, during or after menstruation.

8. The method according to claim 1 wherein the sulfonic acid-containing moiety is selected from:

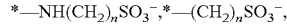

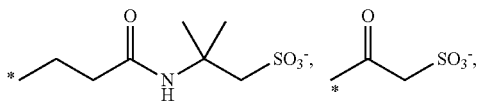

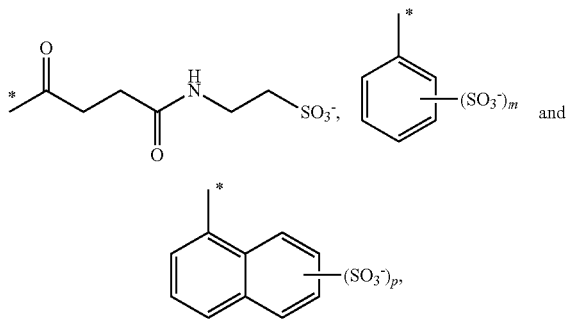

wherein n is zero or is an integer from 1-20, m is an integer 1 or 2 and p is an integer 1 to 3, and * indicates the point of attachment of sulfonic acid-containing moiety to the outermost generation of the dendrimer, optionally by a linker.

9. The method according to claim 8 wherein the sulfonic acid-containing moiety is selected from:

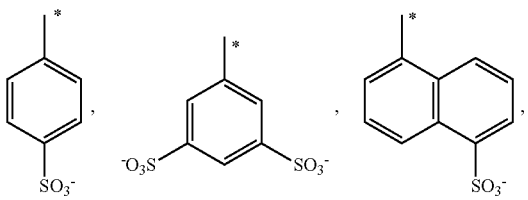

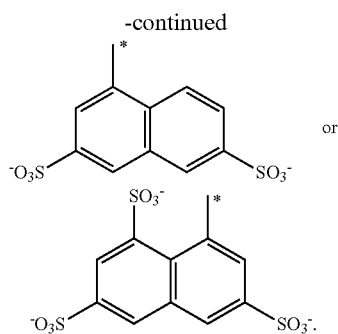

10. The method according to claim 1 wherein the sulfonic acid-containing moiety is attached to the dendrimer terminal amino group by a linker.

11. The method according to claim 10 wherein the linker is an alkylene or alkenylene group in which one or more non-adjacent carbon atoms is optionally with an oxygen or sulfur atom, or a group —X1-(CH2)q-X2- wherein X1 and X2 are independently selected from —NH—, —C(O)—, —O—, —S—, —C(S) and q is 0 or an integer from 1 to 10, and in which one or more non-adjacent (CH2) groups may be replaced with —O— or —S—.

12. The method according to claim 1 wherein the dendrimer has 2-4 generations.

13. The method according to claim 1 wherein the dendrimer is a polylysine dendrimer.

14. The method according to claim 13 wherein the dendrimer is

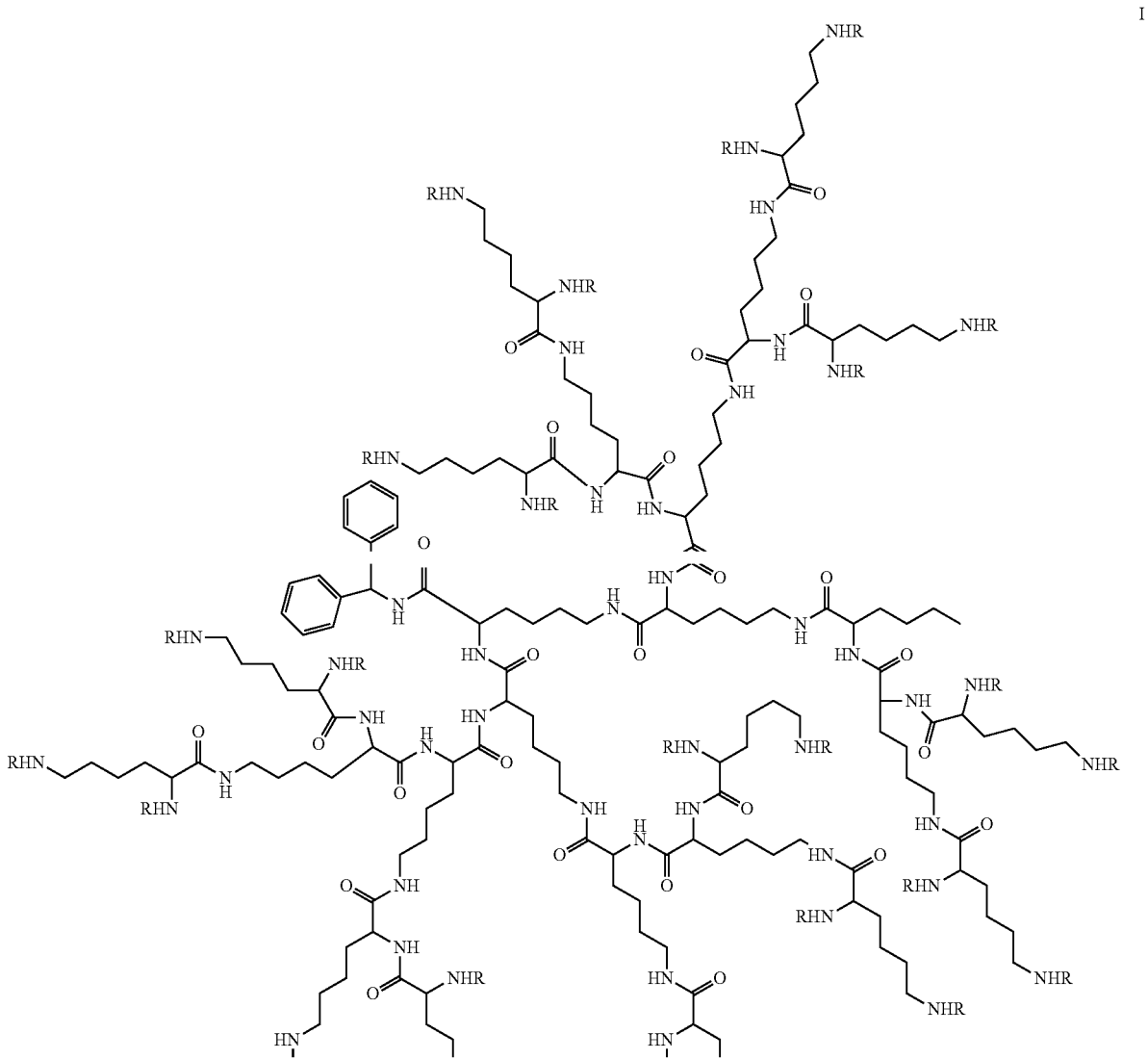

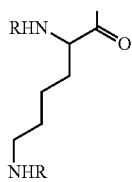

-continued

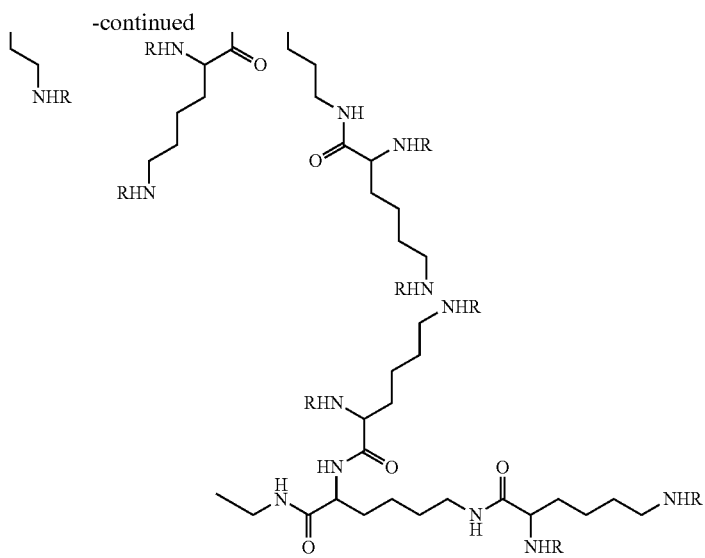

wherein R is

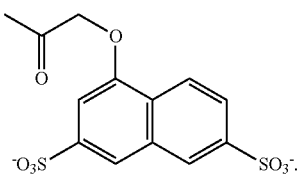

and * indicates the point of attachment of R to the dendrimer.

15. The method according to claim 1 wherein the effective amount is 40 mg to 120 mg per dose.

16. The method according to claim 1 wherein the effective amount is higher than 0.5% (w/w) and less than 3% (w/w) of the macromolecule with relative to a total weight of the composition.

17. The method according to claim 1 wherein the effective amount is 1% (w/w) of the macromolecule with relative to a total weight of the composition.

18. The method according to claim 1 wherein the subject was treated for bacterial vaginosis with antibiotics prior to said administration of the effective amount of the macromolecule.

19. The method according to claim 18 wherein said antibiotics is selected from the group consisting of metronidazole, clindomycin and tinidazole.

20. The method according to claim 18 wherein a Nugent score of the subject, prior to said treatment of the antibiotics, was of 4-10.

21. The method according to claim 1 wherein the macromolecule is administered to a subject presenting with fewer than three of the four following criteria:
  (a) homogeneous white discharge that smoothly coats the vaginal mucosa,
  (b) presence of clue cells,
  (c) vaginal pH of >4.5, and
  (d) positive whiff test.

22. The method according to claim 1 wherein the subject has no clinical symptoms of bacterial vaginosis, prior to said administration of the effective amount of the macromolecule.

23. The method according to claim 1 wherein the subject has no discharge or odor of bacterial vaginosis, prior to said administration of the effective amount of the macromolecule.

* * * * *

UNITED STATES PATENT AND TRADEMARK OFFICE
CERTIFICATE OF CORRECTION

PATENT NO. : 9,155,760 B2
APPLICATION NO. : 13/472953
DATED : October 13, 2015
INVENTOR(S) : Paull et al.

It is certified that error appears in the above-identified patent and that said Letters Patent is hereby corrected as shown below:

Title Page

In column 2 (page 1, item 56) at lines 20-21, Under Other Publications, change "administraction" to --administration--.

In column 1 (page 2, item 56) at line 8, Under Other Publications, change "OO12309," to --0012309,--.

In the Specification

In column 7 at line 35, Change "ssp," to --spp.,--.

In column 7 at line 36, Change "ssp." to --spp.--.

In column 7 at line 37, Change "In a" to --In--.

In column 7 at line 48, Change "ssp," to --spp.,--.

In column 7 at line 51, Change "ssp." to --spp.--.

In column 8 at line 51, Change "clindomycin" to --clindamycin--.

In column 9 at line 4, Change "inguianale)" to --inguinale)--.

In column 9 at line 8, Change "Asperigillus" to --Aspergillus--.

In column 11 at line 40 (approx.), Change "$-NH-(CH_2)_nSO_3^-,-(CH_2)-SO_3^-,$" to -- $-NH-(CH_2)_nSO_3^-, - (CH_2)_n-SO_3^-,$--.

In column 19 at line 66 (approx.), Before "or" insert --10--.

Signed and Sealed this
Seventh Day of June, 2016

Michelle K. Lee
*Director of the United States Patent and Trademark Office*

In the Claims
In column 31 at lines 26-32 (approx.), In Claim 14,
Change " 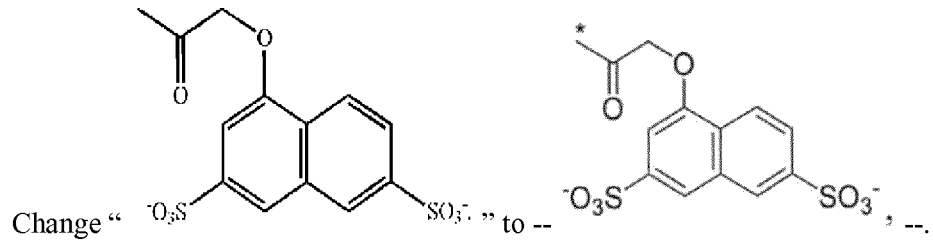 " to -- --.
In column 32 at line 29 (approx.), In Claim 19, change "clindomycin" to --clindamycin--.